(12) United States Patent
Van Den Broek et al.

(10) Patent No.: US 7,159,754 B2
(45) Date of Patent: Jan. 9, 2007

(54) APPARATUS AND METHOD FOR CORRECTIVE SOLDERING

(75) Inventors: Johannes Coleta Maria Van Den Broek, Waalwijk (NL); Lambertus Petrus Christinus Willemen, Dorst (NL); Gerardus Johannes Adrianus Maria Diepstraten, Dongen (NL)

(73) Assignee: Vitronics Soltec B.V. (NL)

( * ) Notice: Subject to any disclaimer, the term of this patent is extended or adjusted under 35 U.S.C. 154(b) by 62 days.

(21) Appl. No.: 10/763,420

(22) Filed: Jan. 26, 2004

(65) Prior Publication Data

US 2004/0200880 A1    Oct. 14, 2004

(30) Foreign Application Priority Data

Jan. 29, 2003    (NL) .................................... 1022515

(51) Int. Cl.
*H01L 2/00* (2006.01)
*B23K 31/12* (2006.01)
*G06K 9/00* (2006.01)
*B23P 21/00* (2006.01)

(52) U.S. Cl. ...................... 228/105; 228/102; 228/103; 228/180.21; 382/145; 382/150; 29/701; 29/720

(58) Field of Classification Search ................ 228/102, 228/103, 104, 180.21; 382/150
See application file for complete search history.

(56) References Cited

U.S. PATENT DOCUMENTS 4,832,250 A * 5/1989 Spigarelli et al. ........... 228/102
4,844,324 A * 7/1989 Todd ...................... 228/180.21
5,145,099 A * 9/1992 Wood et al. .................... 228/9
5,542,600 A * 8/1996 Kobayashi et al. .......... 228/102
RE35,423 E * 1/1997 Adams et al. ................. 378/58
5,657,075 A * 8/1997 Roessner ..................... 348/126
5,680,694 A * 10/1997 Best ............................. 29/701
6,151,380 A * 11/2000 Zweig et al. .................. 378/58
6,681,038 B1 * 1/2004 Vilella ......................... 382/145
6,788,406 B1 * 9/2004 Ross ........................ 356/241.5
2002/0014602 A1   2/2002 Holm et al.
2004/0197019 A1 * 10/2004 Van Den Broek et al. .... 382/150

FOREIGN PATENT DOCUMENTS

JP          4-115146          4/1992
NL          1017843           4/2001

* cited by examiner

*Primary Examiner*—Lynne R. Edmondson
(74) *Attorney, Agent, or Firm*—Banner & Witcoff, Ltd.

(57) ABSTRACT

The invention relates to a method for soldering an object comprising several soldered joints. The method comprises the steps of mechanically soldering of at least some of the soldered joints, visually assessing the soldered joints, and correctively soldering the visually assessed soldered joints that do not meet the relevant quality requirements. The visual assessment takes place by means of a video camera and a computing device connected to the video camera. The assessment criteria for the soldered joints are stored in the computing device. The invention also relates to an apparatus for carrying out the method.

13 Claims, 2 Drawing Sheets

APPARATUS AND METHOD FOR CORRECTIVE SOLDERING

Figure 1:
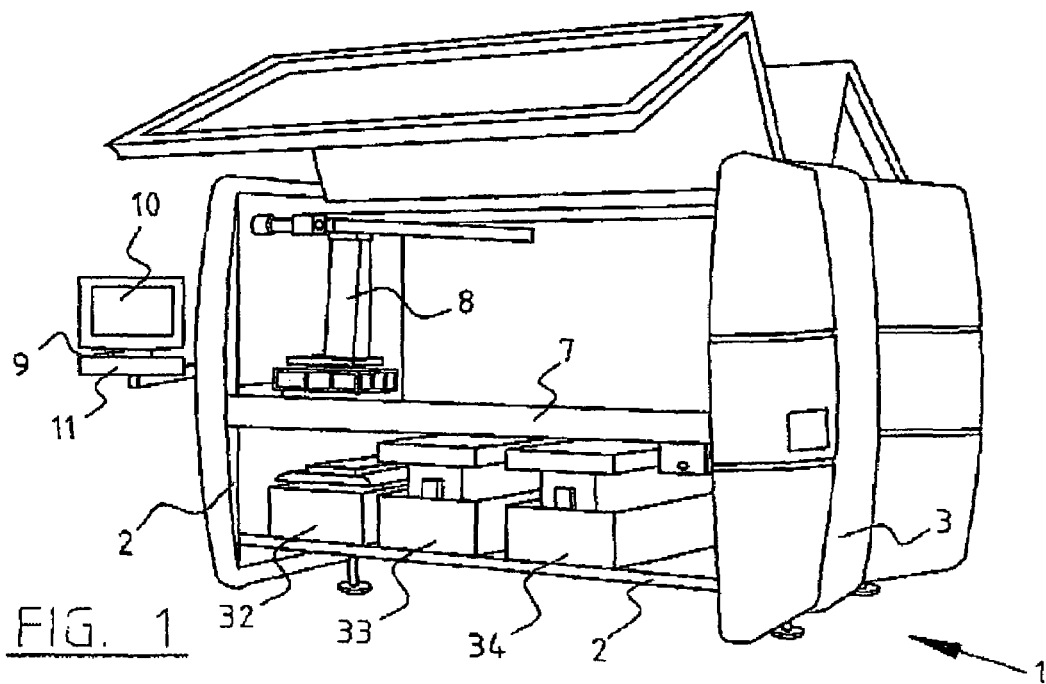

The present invention relates to a method for soldering an object comprising several soldered joints, which method comprises the steps of:

Mechanically soldering of at least some of the soldered joints; visually assessing the soldered joints; and correctively soldering the visually assessed soldered joints that do not meet the relevant quality requirements.

Such a method is generally known. According to this known method, the soldered objects are visually inspected by personnel, and if the person performing the inspection has found that one or more of the soldered joints do not meet the relevant requirements, the soldered joints in question are manually resoldered, for example by means of a soldering iron.

It will be apparent that such a method involves a great deal of human labour, and it is difficult to maintain the relevant quality standards, the more so because the visual checking of the quality of the soldered joints requires expert knowledge.

The object of the present invention is to provide a method of this kind, in which the human assessment factor is eliminated as much as possible, and in which the use of human labour is minimized.

This object is achieved in that said visual assessment takes place by means of a video camera and a computing device connected to the video camera, in which computing device the assessment criteria for the soldered joints are stored.

The result of these aspects is that the assessment criteria are fixed in the memory of the computing device, so that they are reproducible. The human assessment factor is thus eliminated as much as possible.

The object of the invention is also achieved by an apparatus for soldering objects comprising several soldered joints, which apparatus comprises a conveyor for supplying the objects to be soldered and discharging the soldered objects, a soldering device for soldering the objects to be soldered, characterized by a video camera for recording at least one image of at least some of the soldered joints made by the soldering device, and a computing device connected to the video camera for receiving from the video camera signals representing images recorded by the video camera, said computing device being arranged for comparing said signals with signals that are representative of correct soldered joints.

The above aspects eliminate the variation in the human assessment. Nevertheless, the corrective soldering operation still needs to be carried out manually.

This involves a great deal of labour as well, of course, whilst in addition the result is strongly dependent on the manner in which the corrective soldering operation is carried out.

Another object of the present invention is to provide a method and a device in which also the quality of the corrective soldering operation is subject to variation to the smallest possible extent.

This object is achieved by a method in which the corrective soldering of the soldered joints that do not meet the requirements takes place automatically under the control of the computing device.

The object is also achieved by means of an apparatus of the above kind, which comprises a corrective soldering device for the corrective soldering of soldered joints that have been found not to meet the criteria that are stored in the computing device.

Preferably, an apparatus that forms the subject matter of Dutch patent application No. 1017843 is used as the apparatus according to the present invention for carrying out the method according to the present invention.

Preferably, the apparatus according to the present invention is suitable for soldering printed circuit boards. After all, printed circuit boards constitute the major part of the objects to be subjected to a soldering process.

Other advantageous preferred embodiments will become apparent from the other subclaims.

Figure 2:
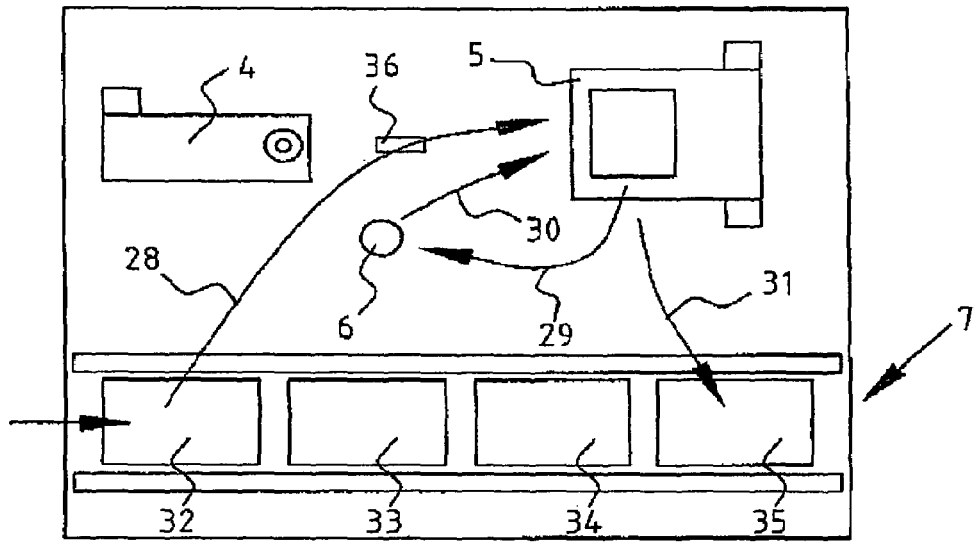
Figure 3:
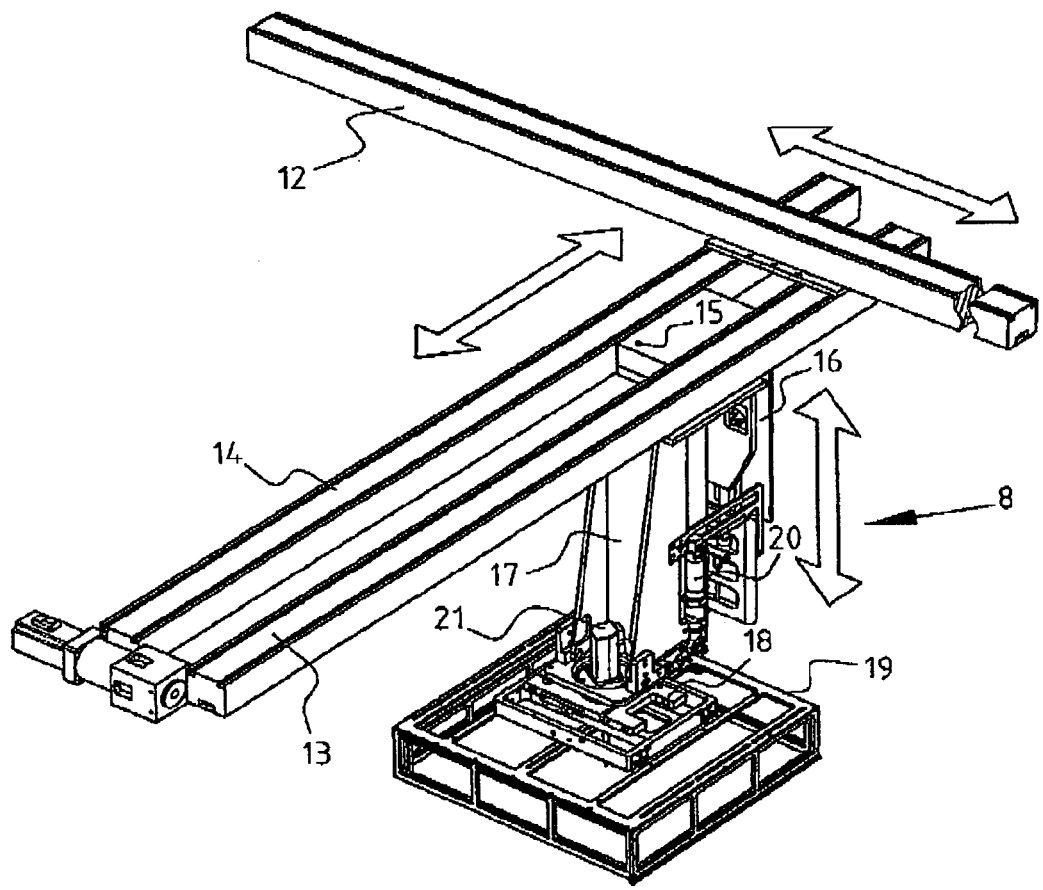
Figure 3:
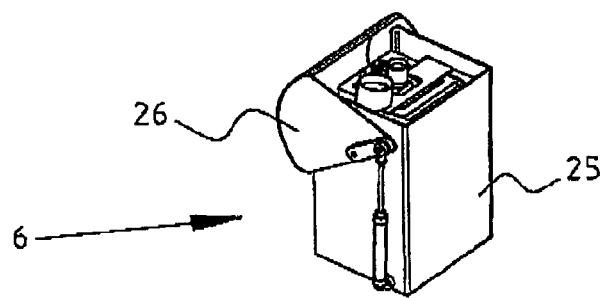

The present invention will now be explained with reference to the appended drawings, which represent in:

FIG. 1: a schematic perspective view of an apparatus according to the present invention, which is preferably used for carrying out the method according to the present invention;

FIG. 2: a horizontal sectional view of the apparatus that is shown in FIG. 2; and FIG. 3: a schematic perspective detail view of the conveying system of the device according to the invention.

In FIG. 1, a soldering machine indicated as a whole by numeral 1 is shown. The soldering machine comprises a frame 2 (schematically shown), on which the housing 3 is mounted, as well as various components forming part of the soldering machine.

Thus, the machine that is shown in FIG. 1 comprises two soldering devices 4,5, preferably of the kind described in Dutch patent application No. 1017843. Said soldering devices are in particular suitable for so-called "selective soldering", i.e. soldering only at positions at which an actual soldered joint is to be made.

It is also possible, however, to substitute at least one of the soldering devices 4,5 as used in the machine according to the invention for a generally known wave soldering machine, which is arranged for soldering the object to be soldered over the entire surface thereof.

The apparatus furthermore comprises a handling device, for example in the form of a robot B. Furthermore, a computing device 9 comprising a display screen 10 and a keyboard 11 is mounted to the outer side of the machine.

The handling device 8 is shown in more detail in FIG. 3. As the Figure shows, the robot system 8 comprises carrying rails extending in the longitudinal direction of the machine, only one of which rails, indicated by numeral 12, is shown. Mounted along said rails are two cross rails 13,14 extending in the transverse direction of the machine, which cross rails are movable in the longitudinal direction along the carrying rails 12. The trolley 15 is connected to an arm 16, which is connected, by means of a linear element (not shown in the drawing), to a construction 17 which extends mainly in vertical direction. Said construction 17 is thus movable in vertical directions with respect to the vertical arm 16.

At the bottom side, the construction 17 is pivotally connected to a supporting plate 18, to which a supporting structure 19 is connected. The supporting plate 18 can be pivoted about a horizontal axis together with the supporting structure 19 by means of a linear operating element 20.

The supporting frame 19 can furthermore be pivoted about a horizontal axis with respect to the construction 17 by means of an electric motor 21. FIG. 3 furthermore shows the camera 6 in more detail. The camera 6 is accommodated in a housing 25, which housing can be closed at its upper side by a movable cover 26. Said cover is important in connection with the fairly fouling environment caused by solder spatter, flux splashes and the like.

Arranged under the conveyor are the successive pre-treatment devices, viz. a fluxer 32 and two pre-heating devices 33, 34. The position 35 is the position from where the soldered objects are transported further.

Now the operation of the apparatus according to the invention will be discussed. Objects to be subjected to the soldering treatment, such as printed circuit boards 27, are supplied on the conveyor 7. The printed circuit boards are picked up from the conveyor 7 by the handling device 8 and subsequently placed on the fluxer 31, where they are provided with flux on their soldered side. Preferably, an inkjet-type spraying device is used for this purpose.

Following that, the objects to be soldered is placed on a pre-heating devices 33 or 34 so as to be heated and subsequently moved to a position above the soldering device 5.

It is noted in this connection that only a single soldering device is used both for "normal" soldering and for corrective soldering in the present case, which device is a device for selective soldering in order that only those soldered joints that were found to be deficient in the preceding quality check are reached during the corrective soldering process. After the object to be soldered has been subjected to the soldering treatment at the soldering device 5, the object is moved to a position above the camera 6. The camera records an image of the entire soldered surface, and the image thus obtained is supplied to the computing device 9 in electronic form.

In the computing device 9 the image, or images if several have been recorded, is subjected to a criteria comparison, which shows whether a number of soldered joints, usually the most critical ones, meet the relevant requirements. If the computing device determines that the soldered joints meet the relevant quality requirements, the handling device will pick up the soldered object 27 and place it back on the conveyor 7.

If, on the other hand, the soldered joints do not meet the requirements, a new soldering operation is carried out. The same soldering device as used in the present embodiment may be used for this purpose, but it is also possible to use a different soldering device. It will be apparent that it is preferred to use a device for selective soldering as described in Dutch patent application No. 1017843 for this corrective soldering. After all, such a device makes it possible to solder only some of the soldered joints.

It is by no means excluded in this connection that it is possible to use a wave soldering machine, for example, for said corrective soldering. In that case, however, re-soldering of the entire object to be soldered is necessary, which constitutes a problem, because it may lead to new soldered joints that do not meet the quality requirements.

In the present embodiment a single soldering device is used both for normal soldering and for corrective soldering. It is also possible, however, to use separate devices for said normal soldering and said corrective soldering. Said "normal soldering" may be carried out by means of a wave soldering machine, for example, whilst said corrective soldering may be carried out by means of a device for selective soldering.

The device for selective soldering furthermore makes it possible to adapt plates to the soldered joints that require corrective soldering, which plates must be adapted to the respective positions to be soldered, of course. After all, a first soldered joint may not meet the quality requirements in a first situation, whilst another joint may not meet the quality requirements when a next soldering operation is carried out. Exchanging the plates in question makes it possible to select the joints to be resoldered.

It is also possible, however, to start from the situation in which a limited number of soldered joints may lead to potential faults. In that case it is sensible to use a plate that is arranged for the resoldering of each of said "difficult" soldered joints.

The above embodiment furthermore comprises a single handling device in the form of a robot construction. It will be apparent that numerous constructions may be used for this purpose, such as different robot-like constructions or entirely different constructions.

The invention claimed is:

1. Method for soldering an object comprising several soldered joints, which method comprises the steps of:
   mechanically soldering of at least some of the soldered joints;
   visually assessing the soldered joints; and
   correctively soldering the visually assessed soldered joints that do not meet relevant quality requirements; wherein the corrective soldering is carried out with a selective soldering device,
   wherein said visual assessment takes place by means of a video camera and a computing device connected to the video camera, wherein the assessment criteria for the soldered joints are stored in the computing device, and wherein the corrective soldering of the soldered joints is carried out with a different soldering device as the mechanical soldering.

2. Method according to claim 1, wherein said corrective soldering of the soldered joints that do not meet the requirements takes place automatically under the control of the computing device.

3. Method according to claim 1, wherein said transport takes place by means of a robot.

4. Method according to claim 1, wherein said apparatus is suitable for soldering printed circuit boards.

5. Apparatus for soldering objects comprising several soldered joints, which apparatus comprises:
   a conveyor for supplying the objects to be soldered and discharging the soldered objects;
   a mechanical soldering device for soldering the objects to be soldered, wherein the mechanical soldering device is a wave soldering device;
   a video camera for recording at least one image of at least some of the soldered joints made by the soldering device;
   a computing device connected to the video camera for receiving from the video camera signals representing images recorded by the video camera, said computing device being arranged for comparing said signals with signals that are representative of correct soldered joints; and
   a corrective soldering device for the corrective soldering of soldered joints that have been found not to meet criteria that are stored in the computing device; wherein the corrective soldering device is a selective soldering device.

6. Apparatus according to claim 5, wherein said corrective soldering device is arranged for the corrective soldering of only those soldered joints that have been found not to meet the criteria.

7. Apparatus according to claim 5, further comprising a handling device for carrying out the following operations under the control of the computing device:

moving the objects to be soldered from the conveyor to the soldering device;

moving the soldered objects from the soldering device to a position within the recording area of the video camera;

moving the soldered objects from the recording area of the video camera to the conveyor; and moving the soldered objects from the video camera to and from the corrective soldering device, if the image recorded by the video camera does not meet the criteria that are stored in the computing device.

8. Apparatus according to claim 7, wherein said handling device is a robot controlled by the computing device.

9. Apparatus according to claim 5, wherein the apparatus is suitable for handling printed circuit boards.

10. Apparatus according to claim 5, wherein said corrective soldering device is arranged for soldering only a single soldered joint or a single group of soldered joints under the control of the computing device.

11. Apparatus according to claim 10, wherein said handling device is suitable for exchanging masking plates under the control of the computing device.

12. Method according to claim 1, wherein the mechanical soldering is carried out with a wave soldering device.

13. Method according to claim 1, wherein the mechanical soldering is carried out with a selective soldering device.

* * * * *